(12) United States Patent
Krueger

(10) Patent No.: US 6,520,946 B1
(45) Date of Patent: Feb. 18, 2003

(54) PREFOLDED PREFASTENED INCONTINENCE GARMENT WITH EXPANDIBLE BELLOWS

(75) Inventor: Gary A. Krueger, Neenah, WI (US)

(73) Assignee: Kimberly-Clarke Worldwide, Inc., Neenah, WI (US)

( * ) Notice: Subject to any disclaimer, the term of this patent is extended or adjusted under 35 U.S.C. 154(b) by 0 days.

(21) Appl. No.: 09/604,389

(22) Filed: Jun. 27, 2000

(51) Int. Cl.$^7$ ................................................ A61F 13/15
(52) U.S. Cl. ...................... 604/386; 604/387; 604/389; 604/396
(58) Field of Search .................... 604/386, 387, 604/389, 390, 391, 396; 206/440, 439, 823, 812

(56) References Cited

U.S. PATENT DOCUMENTS

| | | | |
|---|---|---|---|
| 4,578,072 A | * | 3/1986 | Lancaster ................ 604/385 A |
| 4,585,450 A | * | 4/1986 | Rosch et al. ................. 604/390 |
| 5,607,537 A | | 3/1997 | Johnson et al. |
| 5,622,589 A | | 4/1997 | Johnson et al. |
| 5,624,428 A | * | 4/1997 | Sauer .......................... 604/391 |
| 5,643,396 A | | 7/1997 | Rajala et al. |
| 5,660,679 A | | 8/1997 | Rajala et al. |
| 6,022,432 A | * | 2/2000 | Elsberg et al. .............. 156/73.1 |
| 6,036,805 A | * | 3/2000 | McNichols .................. 156/227 |

* cited by examiner

Primary Examiner—John G. Weiss
Assistant Examiner—Jacqueline F Stephens
(74) Attorney, Agent, or Firm—Pauley Petersen Kinne & Erickson

(57) ABSTRACT

A nonwoven, disposable, incontinence garment, such as a diaper, has refastenable attachment means, such as a hook and look fastening system for attaching the front panel to the back panel. The garment is packaged in its point of sale container with the attachment means prefastened so that it can be used immediately as a pull on garment and then removed in the manner of a diaper. The attachment means of the rear panel includes extra material which is folded on itself and lightly bonded at the folds to provide simple in-process execution of a permanent lap bond between the attachment means and the rear panel which will not separate during use of the garment. The attachment means of the front panel includes extra material which is folded on itself and lightly bonded at the folds to also provide extra expansion of the diaper. The extra material of the rear attachment means is also lightly bonded to the extra material of the front attachment means to provide extra expansion of the diaper and provide in-process handling advantages.

6 Claims, 3 Drawing Sheets

US 6,520,946 B1

PREFOLDED PREFASTENED INCONTINENCE GARMENT WITH EXPANDIBLE BELLOWS

FIELD OF THE INVENTION

The present invention relates generally to means for making diapers, or other undergarments, especially as related to incontinence products. The present invention relates specifically to a diaper which is prefastened in its point of sale container so that the diaper may be used as a pull-on type training pant but may be removed like a regular diaper by separating the front and rear waist portions through disengaging the refastenable fastening means holding the front and rear together. The present invention relates even more specifically to a method of making such prefastened diapers when the diapers are laid out as in-process or precursor diapers, on a web, with their long axes in the cross machine, or cross, direction of the web.

DISCUSSION OF THE RELATED ART

In the known art, there have been two ways of making the diaper web into point of sale items. One is to put refastenable tabs, such as adhesive tape or hook and loop combinations onto the diaper body, in the manner of an infant diaper, for later use to secure the back panel of the diaper to the front panel. A second is to bond the side edges of the front and back waist sections together to make a fixed waist band, in the manner of a training pant which is slid on and off the wearer like a regular adult garment. To remove such a garment if it becomes soiled it is necessary to break the waist band bond in order to remove the garment like a diaper, as convenience and hygiene would dictate.

It is therefore desired to provide a training pant which may be slid-on in the fashion of an adult garment while being easily removeable in the manner of a diaper and which is made with relatively uncomplicated machinery.

SUMMARY OF THE INVENTION

In order to satisfy this need the present invention provides a nonwoven, disposable, incontinence garment, such as a diaper, which has refastenable attachment means, such as a hook and look fastening system, for attaching the front panel of the garment to the back panel. The garment is packaged in its point of sale container with the attachment means prefastened so that it can be used immediately as a pull on garment and then removed in the manner of a diaper if so desired. The garment is provided with expansion capability in the area of the fastening system and has in-process bonds which aid in ease of manufacture and use of the garment.

Within the primary attachment means of the refastenable system is additional material which is folded and lightly bonded to itself. The lightly bonded folds provide a bellows of extra material which will expand to provide the larger wearer extra comfort. The attachment means of the rear panel includes extra material which is folded on itself and lightly bonded at the folds to provide an in-process configuration allowing for a more secure bond to be accomplished between the attachment means and the rear panel. The light bonds are not intended to withstand more than a minimal amount of strain, such as the strain of in-process handling. The strain of a wearer pulling on the garment against resistance of the body mass is intended to part the light bonds.

The attachment means of the front panel includes extra material which is folded on itself and lightly bonded at the folds to also provide extra expansion of the diaper. The extra material of the rear attachment means is also lightly bonded to the extra material of the front attachment means to provide extra expansion of the diaper and provide in-process handling advantages. The light bond of the front material to the material of the rear panel attachment means may be made slightly stronger than the other light bonds but is intended to give under a small amount of strain deliberately applied in an effort to remove the garment in the manner of a diaper.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
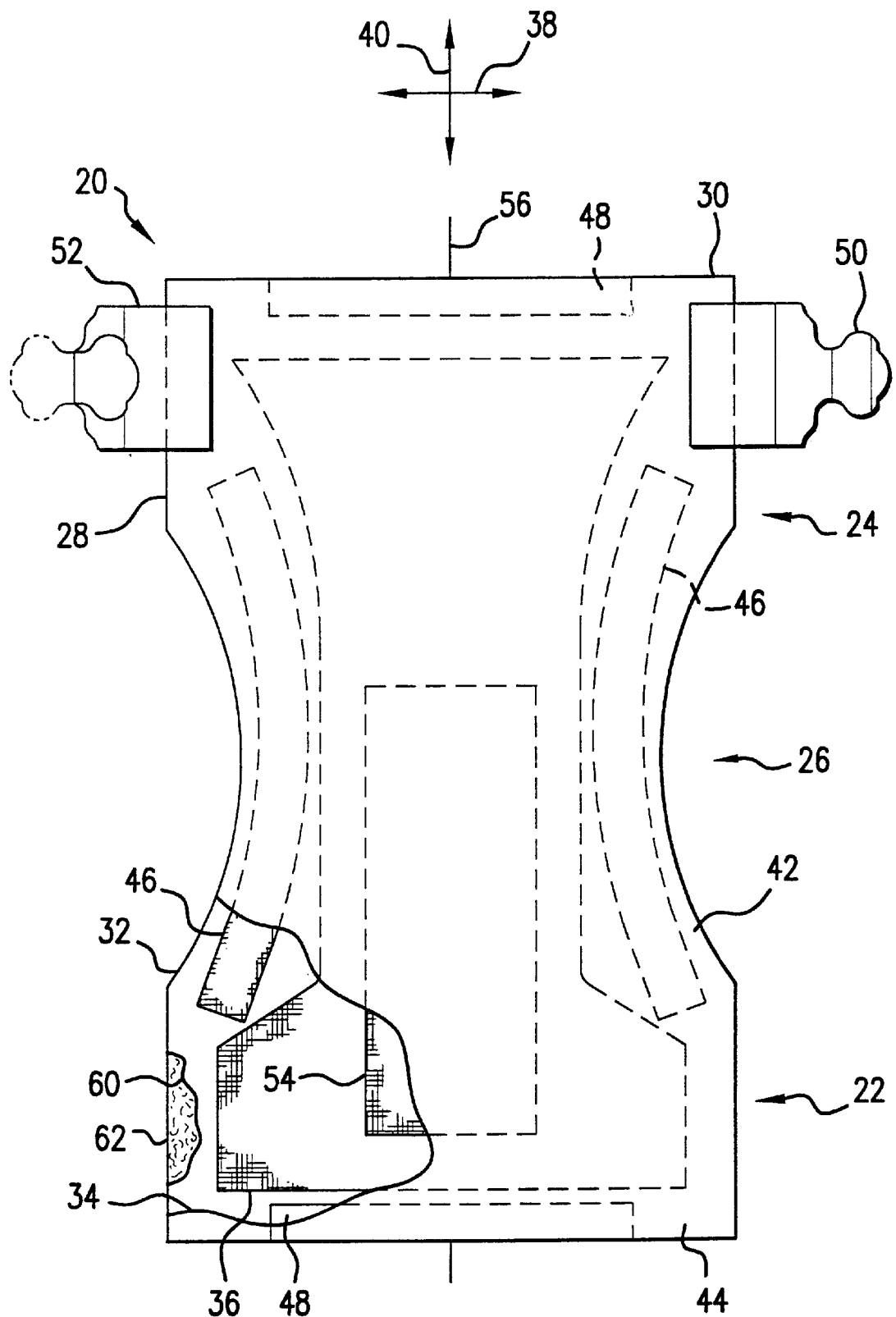
FIG. 1 is a view of a laid open, fully extended, partially cut away top plan view of a known absorbent article, or diaper, useful for teaching the parts thereof as an aid to understanding the present invention.

With reference to FIG. 1, an absorbent garment, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable, vapor permeable, composite backsheet 32, a porous, liquid permeable topsheet 34 positioned in facing relation with the backsheet 32, and an absorbent body 36, such as an absorbent pad, which is located between the backsheet and the topsheet. The diaper 20 also has a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The diaper 20, as representatively illustrated in FIG. 1, may further include a fastening system 49 illustrated by a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20. In the case of training pants, additional web material may be added to the fastening system 49 and arranged under the fasteners 50 to be lightly bonded to the front waist section 22 to provide a more pant-like feel and yet be easily broken away to permit removal like a diaper. The various components of the diaper 20 are assembled together employing various types of suitable attachment means, such as adhesive, sonic bonds, thermal bonds or combinations thereof.

Figure 2:
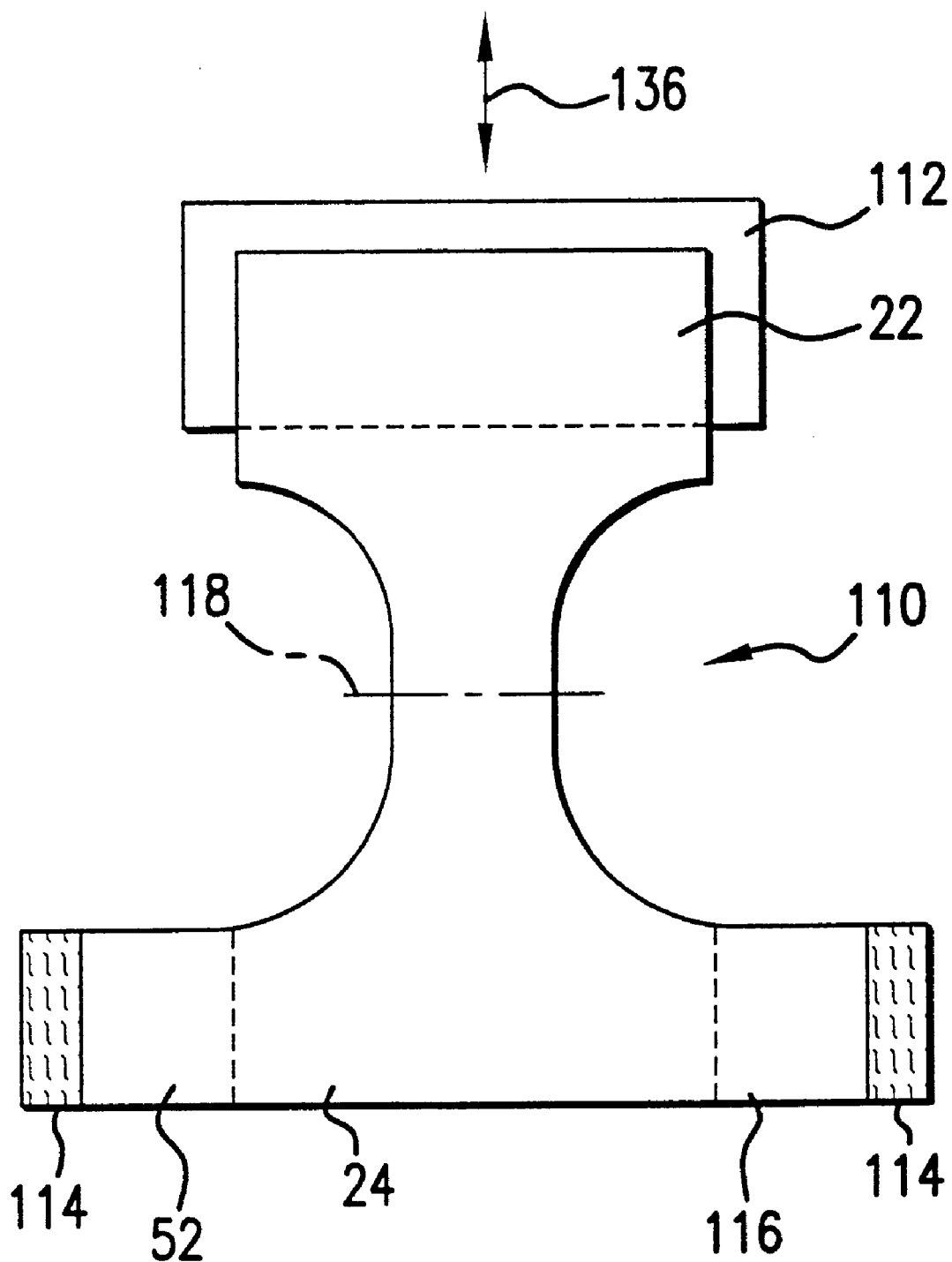
FIG. 2 is a highly schematic view of a laid open diaper with a hook and loop fastening system which may be processed according to the present invention.

Referencing FIG. 2, the interior view of a laid open diaper 110 is shown with front waist section 22 having attached thereto, or incorporated therein, a panel of loop material 112, the loops thereof are facing forward on the diaper, as judged from the perspective of the wearer, and therefore are not visible. While shown as one panel it will be appreciated that one or more loop material panels may be selectively placed on the front waist section 22. The rear waist section 24 has attached at its right and left lateral edges, or side margins, hook material 114. The lateral edges may be material 116 extended from the back sheet or other material of the diaper 110 or the hook material 114 may be extended from the lateral edges of the back sheet with cooperating side panels 52 in the manner of FIG. 1 without sacrifice of functionality in regard to the present invention. Together the loop material 112 and the hook material 114 represent the first and second cooperative fastening means of the primary fastening system of the diaper for joining the front waist section 22 to the rear waist section 24 when the diaper 110 is folded about its medial line 118 perpendicular to the longitudinal axis of the diaper. The primary fastening means is selectively fastenable and unfastenaable, this arrangement sometimes being referred to as "refastenable".

Figure 3:
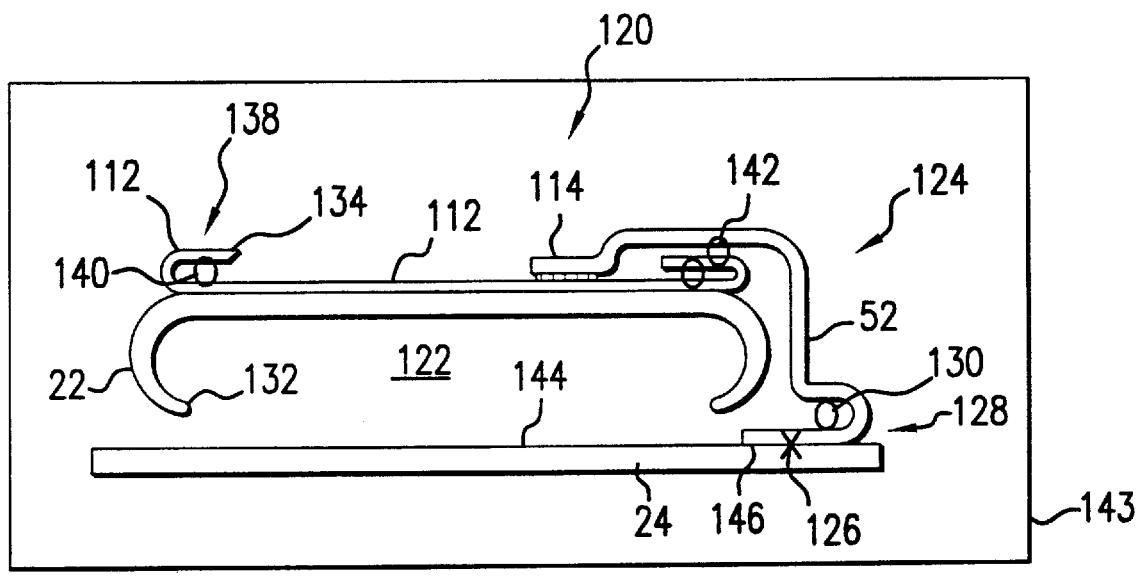
FIG. 3 is an end view looking into the waist band area of a folded and fastened diaper according to the present invention with the portions of the diaper expanded from each other, rather than flattened as they would be during in-process construction, for ease of illustration.

Referencing FIG. 3, the present invention is shown from the perspective of an end view of a folded and prefastened diaper 120 looking at the waist band area and into the body cavity or interior 122 of the diaper 120. Only one hook fastener and cooperating side panel assembly 124 is shown for clarity of illustration.

Figure 4:
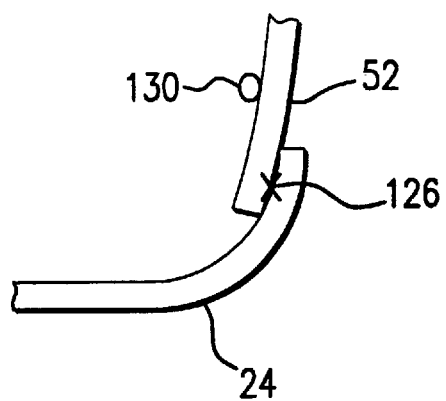
FIG. 4 is a detail view of the bond between the rear panel of the diaper and its primary attachment means once the diaper has been expanded by placing the diaper onto the wearer.

The hook fastener and cooperating side panel assembly 124 has hook material 114 at a first end thereof. At a second or opposite end, the cooperating side panel 52 is permanently bonded to the rear waist section 24 indicated at the "x" of reference number 126. A portion 128 of the cooperating side panel 52 is folded on itself in a "J" loop and lightly bonded at the folds thereof, as indicated at the "o" of reference number 130. The light bond 130 will break away when placed under minimal stress above the level of in-process manufacturing stresses. Examples of bonding technology for folded materials in incontinence garments may be seen at, e.g. U.S. Pat. Nos. 5,607,537 and 5,622,589. It will be appreciated that more than one fold, and different locations and configurations of folds, may be utilized as desired. By placing the short leg 146 of the "J"-loop 128 flat against the inside surface 144 of the flattened back waist section 24 and permanently bonding the two members, a permanent bond is more easily accomplished which is loaded in shear when the light bond 130 is broken under the stress of applying the diaper to the wearer, as best seen in FIG. 4. If a simple butt joint or flange joint were used, the seam, or bond, would be more easily separated possibly resulting in a failure of the diaper.

The front waist section 22 will typically, although not necessarily, have its lateral edges 132 folded rearwardly and towards the interior 122 of the diaper when the diaper is folded to make the prefastened garment product. A loop material panel 112 has its lateral edges 134 free of attachment to the front waist section 22 and folded forwardly and towards the longitudinal axis 136 of the laid open diaper (FIG. 2). The portion 138 of the loop panel 112 folded on itself is lightly bonded, indicated by the "o" at reference number 140 to provide a second expandible bellows for the comfort of the larger wearer.

The cooperating side panel 52 is wrapped towards the front waist section 22 in order that the hook material 114 is fastened into the loop material 112 at a point beyond the folded loop material portion 138 to prefasten the diaper 120. At a point where the cooperating side panel 52 transits the folded portion 138 of the loop material, the cooperating side panel is lightly bonded to the loop material, as indicated by the "o" at reference number 142 so that the front waist section 22 does not fold into the interior 122 of the diaper 120 during processing thus maintaining integrity of the garment during manufacturing and also, if desired, during application of the garment to the wearer. The prefolded, prefastened diaper is then inserted into a point of sale container 143 such as a box, bag, or the like for distribution to the end user.

While the embodiments disclosed herein are presently considered to be preferred, various modifications and improvements can be made without departing from the spirit and scope of the invention. The scope of the invention is indicated by the appended claims, and all changes that fall within the meaning and range of equivalents are intended to be embraced therein.

I claim:

1. A packaged prefastened incontinence garment comprising:

a. a front waist section of the garment and a rear waist section of the garment, one of the front waist section of the garment and a rear waist section of the garment including an area having a first panel with first fastening means and with edges folded outwardly of the garment and toward a longitudinal centerline of the garment;

b. a second panel with second fastening means for cooperatively engaging the first fastening means, the second fastening means being permanently bonded to one of the front waist section of the garment and a rear waist section of the garment;

c. a portion of a garment section attached to the second fastening means being folded on itself with a weak bond holding the folded portions thereof;

d. the garment section attached to the second fastening means being weakly bonded to the outwardly folded edges of the first panel;

e. the first and second fastening means being cooperatively engaged to create a prefastened diaper; and f. the prefastened diaper being packaged in a point of sale container.

2. A packaged prefastened incontinence garment comprising:

a. a front waist section of the garment and a rear waist section of the garment, one of the front waist section of the garment and a rear waist section of the garment including an area having a first panel with first fastening means and with edges folded outwardly of the garment and toward a longitudinal centerline of the garment;

b. a second panel with second fastening means for cooperatively engaging the first fastening means and having a cooperating side panel attached thereto, the cooperating side panel permanently bonded to one of the front waist section of the garment and a rear waist section of the garment;

c. the cooperating side panel folded on itself with a weak bond holding the folded portions thereof;

d. the cooperating side panel weakly bonded to the outwardly folded edges of the first panel;

e. the first and second fastening means being cooperatively engaged to create a prefastened diaper; and f. the prefastened diaper being packaged in a point of sale container.

3. The prefastened incontinence garment according to claim 2 further comprising:

the first fastening means being a loop material, and the second fastening means being a hook material.

4. The prefastened incontinence garment according to claim 2 further comprising:

the first fastening means being attached to the front waist section, and the second fastening means being attached to the rear waist section.

5. The prefastened incontinence garment according to claim 3 further comprising:

the loop material being attached to the front waist section, and the hook material being attached to the rear waist section.

6. A packaged prefastened refastenable incontinence garment comprising:

a. a front waist section with lateral edges folded rearward toward an interior of the garment;

b. a loop material panel with lateral edges folded forward and toward a longitudinal centerline of the garment, the folded portion of the loop material being weakly bonded to itself, the loop material panel being permanently bonded to the front waist section;

c. a hook fastener and cooperating side panel assembly, the cooperating side panel permanently bonded to a rear waist section of the garment;

d. the cooperating side panel folded on itself with a weak bond holding the folded portions thereof;

e. the cooperating side panel being weakly bonded to the forward fold of the loop material panel;

f. the hook fastener embedded in the loop material panel to create a prefastened diaper; and g. the prefastened diaper being packaged in a point of sale container.

* * * * *